(12) United States Patent
Nakashima et al.

(10) Patent No.: US 8,609,321 B2
(45) Date of Patent: Dec. 17, 2013

(54) RADIATION-SENSITIVE RESIN COMPOSITION, POLYMER AND COMPOUND

(71) Applicant: JSR Corporation, Tokyo (JP)

(72) Inventors: Hiromitsu Nakashima, Tokyo (JP); Reiko Kimura, Tokyo (JP); Kazuo Nakahara, Tokyo (JP); Mitsuo Sato, Tokyo (JP)

(73) Assignee: JSP Corporation, Tokyo (JP)

( * ) Notice: Subject to any disclaimer, the term of this patent is extended or adjusted under 35 U.S.C. 154(b) by 0 days.

(21) Appl. No.: 13/789,701

(22) Filed: Mar. 8, 2013

(65) Prior Publication Data

US 2013/0189621 A1    Jul. 25, 2013

Related U.S. Application Data

(63) Continuation of application No. PCT/JP2011/070401, filed on Sep. 7, 2011.

(30) Foreign Application Priority Data

Sep. 9, 2010  (JP) .................................. 2010-201716

(51) Int. Cl.
  *G03F 7/038*  (2006.01)
  *G03F 7/039*  (2006.01)
(52) U.S. Cl.
  USPC ........ 430/270.1; 430/910; 430/907; 430/914; 430/311; 430/325; 430/326; 526/282; 526/284; 560/176; 560/205; 560/217; 560/220; 560/227
(58) Field of Classification Search
  None
  See application file for complete search history.

(56) References Cited

FOREIGN PATENT DOCUMENTS

| JP | 11-012325 | 1/1999 |
|---|---|---|
| JP | 11-015164 | 1/1999 |
| JP | 11-035848 | 2/1999 |
| JP | 2005-238816 | 9/2005 |
| JP | 2006-171667 | 6/2006 |
| JP | 2006-227632 | 8/2006 |
| JP | 2007-284381 | 11/2007 |
| WO | WO 2005/069076 | 7/2005 |
| WO | WO 2006/035790 | 4/2006 |

OTHER PUBLICATIONS

International Search Report for corresponding International Application No. PCT/JP2011/070401, Oct. 11, 2011.

*Primary Examiner* — Sin Lee
(74) *Attorney, Agent, or Firm* — Ditthavong Mori & Steiner, P.C.

(57) ABSTRACT

A radiation-sensitive resin composition includes a polymer having a structural unit represented by a formula (I). In the formula (I), $R^1$ represents a hydrogen atom or a methyl group. X represents a bivalent alicyclic hydrocarbon group not having or having a substituent. Y represents a bivalent hydrocarbon group having 1 to 20 carbon atoms. $R^2$ represents a methyl group or a trifluoromethyl group.

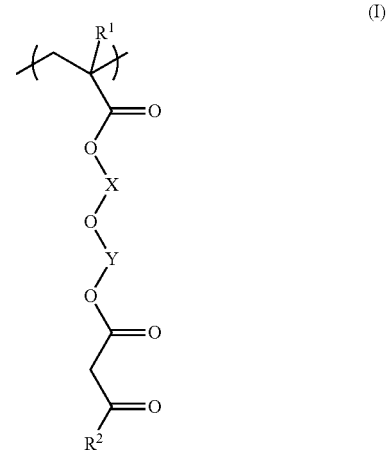

5 Claims, No Drawings

RADIATION-SENSITIVE RESIN COMPOSITION, POLYMER AND COMPOUND

CROSS-REFERENCE TO RELATED APPLICATIONS

The present application is a continuation application of International Application No. PCT/JP2011/070401, filed Sep. 7, 2011, which claims priority to Japanese Patent Application No. 2010-201716, filed Sep. 9, 2010. The contents of these applications are incorporated herein by reference in their entirety.

BACKGROUND OF THE INVENTION

1. Field of the Invention

The present invention relates to a radiation-sensitive resin composition, and a polymer and a compound.

2. Discussion of the Background

In the microfabrication field typified by manufacturing processes of semiconductors in recent years, photolithography has been investigated in which a radioactive ray having a short wavelength typified by an ArF excimer laser (wavelength: 193 nm) is used. Known materials for use in such photolithography include radiation-sensitive resin compositions that generate an acid by irradiation with the radioactive ray at a light-exposed site, and thus a resist pattern is formed on a substrate by producing a difference in rates of dissolution in a developer solution between light-exposed sites and light-unexposed sites due to a catalytic action of the acid.

As materials of radiation-sensitive resin compositions for which an ArF excimer laser is used as a light source, a polymer having an alicyclic hydrocarbon group in its skeleton chain is frequently used due to not having a great absorption in a region of 193 nm and having high etching resistance. Of these, in light of improvement of line edge roughness, a structure having a 1,3-diketone skeleton has been proposed (see Japanese Unexamined Patent Application, Publication No. 2006-171667). Furthermore, in light of attaining both developability and etching resistance, a structure in which the 1,3-diketone skeleton is substituted with a (meth)acryl-substituted adamantanol skeleton has been proposed (see Japanese Unexamined Patent Application, Publication No. 2007-284381).

SUMMARY OF THE INVENTION

According to one aspect of the present invention, a radiation-sensitive resin composition includes a polymer having a structural unit represented by a formula (I).

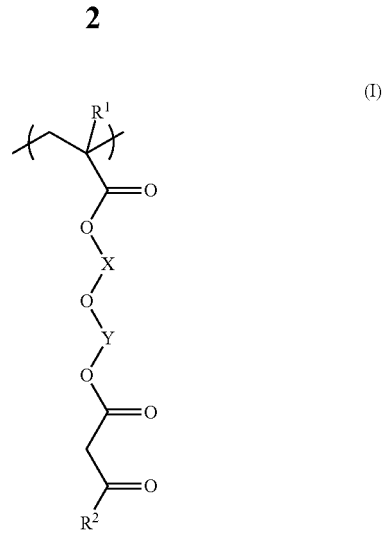

In the formula (I), $R^1$ represents a hydrogen atom or a methyl group. X represents a bivalent alicyclic hydrocarbon group not having or having a substituent. Y represents a bivalent hydrocarbon group having 1 to 20 carbon atoms. $R^2$ represents a methyl group or a trifluoromethyl group.

According to another aspect of the present invention, a polymer includes a structural unit represented by a formula (I).

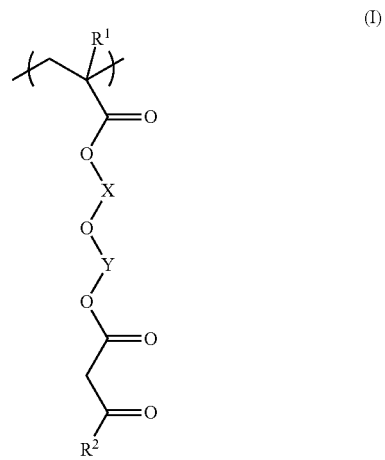

In the formula (I), $R^1$ represents a hydrogen atom or a methyl group. X represents a bivalent alicyclic hydrocarbon group not having or having a substituent. Y represents a bivalent hydrocarbon group having 1 to 20 carbon atoms. $R^2$ represents a methyl group or a trifluoromethyl group.

According to further aspect of the present invention, a compound is represented by a formula (i).

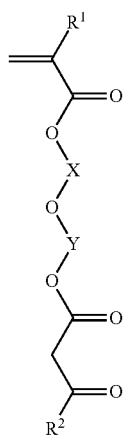

(i)

In the formula (i), $R^1$ represents a hydrogen atom or a methyl group. X represents a bivalent alicyclic hydrocarbon group not having or having a substituent. Y represents a bivalent hydrocarbon group having 1 to 20 carbon atoms. $R^2$ represents a methyl group or a trifluoromethyl group.

DESCRIPTION OF THE EMBODIMENTS

A radiation-sensitive resin composition according to an aspect of the embodiment of the present invention made for solving the foregoing problems contains (A) a polymer (hereinafter, may be also referred to as "polymer (A)") having a structural unit represented by the is following formula (I) (hereinafter, may be also referred to as "structural unit (1)"):

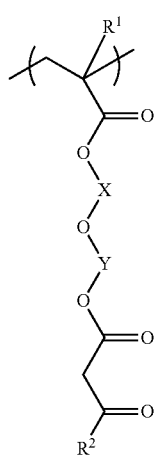

(I)

in the formula (I), $R^1$ represents a hydrogen atom or a methyl group; X represents a bivalent alicyclic hydrocarbon group not having or optionally having a substituent; Y represents a bivalent hydrocarbon group having 1 to 20 carbon atoms; and $R^2$ represents a methyl group or a trifluoromethyl group.

The radiation-sensitive resin composition contains the polymer (A). It is believed that a bivalent alicyclic hydrocarbon group and a diketone skeleton in the structural unit (1) included in the polymer (A) is responsible for improvement of rigidity. As a result, the radiation-sensitive resin composition is superior in an LWR property. In addition, due to having a linking group represented by Y in the structural unit (1), the side chain has appropriate flexibility, thereby making the diketone skeleton likely to be brought into contact with an alkaline developer solution to improve an affinity of the polymer (A) to the alkaline developer solution, and consequently the radiation-sensitive resin composition can suppress generation of defects. It is to be noted that the term "structural unit" as referred to herein means one unit included in a polymer structure, and may be repeatedly included.

Y in the above formula (I) preferably represents an alkanediyl group having 2 to 4 carbon atoms. When Y represents the group specified above and have an appropriate chain length, it is believed that rigidity of the polymer (A) and flexibility of the side chain can be both attained at more appropriate levels, and as a result, an LWR property of the radiation-sensitive resin composition can be improved and generation of defects can be further suppressed.

It is preferred that the radiation-sensitive resin composition further contains (B) a radiation-sensitive acid generator (hereinafter, may be also referred to as "acid generator (B)"). When the radiation-sensitive resin composition further contains the acid generator (B), higher sensitivity to radioactive rays can be attained.

A polymer according to another aspect of the embodiment of the present invention has a structural unit represented by the following formula (I):

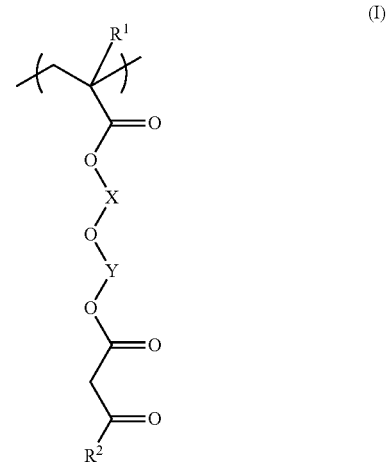

(I)

in the formula (I), $R^1$ represents a hydrogen atom or a methyl group; X represents a bivalent alicyclic hydrocarbon group not having or optionally having a substituent; Y represents a bivalent hydrocarbon group having 1 to 20 carbon atoms; and $R^2$ represents a methyl group or a trifluoromethyl group.

Since the polymer has the features described above, it can be suitably used for a radiation-sensitive resin composition, etc., used in, for example, lithography techniques.

A compound according to other aspect of the embodiment of the present invention is represented by the following formula (i):

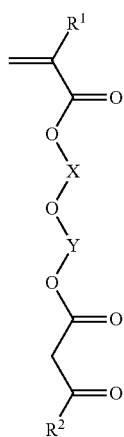

in the formula (i), $R^1$ represents a hydrogen atom or a methyl group; X represents a bivalent alicyclic hydrocarbon group not having or optionally having a substituent; Y represents a bivalent hydrocarbon group having 1 to 20 carbon atoms; and $R^2$ represents a methyl group or a trifluoromethyl group.

Since the compound has the structure described above, it can be suitably used as, for example, a monomer that gives the polymer.

According to the aspects of the embodiments of the present invention, a radiation-sensitive resin composition being superior in an LWR property and capable of suppressing generation of defects, and a polymer and a compound suitably used for the composition and the like can be provided. Therefore, when used as a chemically amplified type radiation-sensitive resin composition that is sensitive to actinic radiation of a short wavelength, products with superior process margin in microfabrication can be manufactured. Therefore, these can be suitably used in the field of integrated circuit elements and the like in which microfabrication is expected to further advance in the future.

Hereinafter, embodiments of the present invention will be explained in detail.

Radiation-Sensitive Resin Composition

A radiation-sensitive resin composition according to an embodiment of the present invention may contain (A) a polymer, and further as needed (B) an acid generator and optional component(s). According to a concept of the "radioactive ray" in connection with the "radiation-sensitive resin composition" and the "radiation-sensitive acid generator" as referred to herein, visible light rays, ultraviolet rays, far ultraviolet rays, X-rays, charged particles and the like are involved. Hereinafter, the polymer (A), the acid generator (B) and the optional components are explained in detail.

(A) Polymer

The polymer (A) includes a polymer having a structural unit (1). The polymer (A) has a solubility in a developer solution which will be altered by an acid generated from the acid generator (B) or the like contained in the radiation-sensitive resin composition upon exposure. In the case in which the polymer (A) has an acid-dissociable group described later (hereinafter, may be also referred to as "polymer (A1)"), the polymer that is originally insoluble or hardly soluble in an alkali and is soluble in an organic solvent, but altered to be soluble in an alkali and be insoluble or hardly soluble in an organic solvent by an action of an acid. Also, when the polymer (A) does not substantially have an acid-dissociable group (hereinafter, may be also referred to as "polymer (A2)"), and a crosslinking agent is contained in the composition, the polymer that is originally soluble in an alkali and insoluble or hardly soluble in an organic solvent altered to be a polymer that is insoluble or hardly soluble in an alkali and soluble in the organic solvent as a result of crosslinkage by an action of an acid.

It is to be noted that the phrase "insoluble or hardly soluble in an alkali (organic solvent)" as referred to herein means a feature found when a coating film provided using only the polymer (A) in place of a resist coating film is developed under a condition of development with an alkali (organic solvent) employed in forming a resist pattern from a resist coating film provided using the radiation-sensitive resin composition, no less than 50% of the initial film thickness of the that coating film remains after development.

The polymer (A) may have in addition to the structural unit (1), a structural unit (2) for including an acid-dissociable group in the polymer (A) and a structural unit (3) for including a lactone structure and/or a cyclic carbonate structure, and other structural unit.

Structural Unit (1)

The structural unit (1) is represented by the above formula (I).

In the above formula (I), $R^1$ represents a hydrogen atom or a methyl group; X represents a bivalent alicyclic hydrocarbon group not having or optionally having a substituent; Y represents a bivalent hydrocarbon group having 1 to 20 carbon atoms; and $R^2$ represents a methyl group or a trifluoromethyl group.

Examples of the bivalent alicyclic hydrocarbon group not having or optionally having a substituent represented by X include monocyclic alicyclic hydrocarbon groups such as a cyclobutanediyl group, a cyclopentanediyl group, a cyclohexanediyl group and a cyclooctanediyl group; bivalent bridged alicyclic hydrocarbon groups such as a norbornanediyl group, a tricyclodecanediyl group, a tetracyclododecanediyl group and an adamantanediyl group, and the like.

Of these, X represents preferably a bivalent bridged alicyclic hydrocarbon group, and more preferably an adamantanediyl group.

Examples of the bivalent hydrocarbon group having 1 to 20 carbon atoms represented by Y include:

bivalent linear or branched hydrocarbon groups having 1 to 20 carbon atoms such as a methanediyl group, an ethanediyl group, a n-propanediyl group, an i-propanediyl group, a n-butanediyl group, a n-pentanediyl group and a n-hexanediyl group;

bivalent alicyclic hydrocarbon groups having 3 to 20 carbon atoms such as a cyclobutanediyl group, a cyclopentanediyl group, a cyclohexanediyl group, a cyclooctanediyl group, a norbornanediyl group, a tricyclodecanediyl group, a tetracyclododecanediyl group and an adamantanediyl group;

arylene group having 6 to 20 carbon atoms such as a phenylene group and a naphthylene group;

arylenealkylene group having 7 to 20 carbon atoms such as a benzylene group, a phenyleneethylene group, a phenylenepropylene group and a naphthylene methylene group, and the like.

Of these, Y represents more preferably an alkanediyl group having 1 to 4 carbon atoms, an ethanediyl group, a propanediyl group or a butanediyl group, and particularly preferably an ethanediyl group. When Y represents a group having a chain length falling within a more preferred range, it is believed that rigidity of the polymer (A) and flexibility of the side chain can be both attained at more appropriate levels. As a result, an LWR property of the radiation-sensitive resin composition can be improved, and generation of defects can be further suppressed.

Examples of the structural unit (1) include structural units represented by the following formulae (I-1) to (I-18), and the like. Of these, structural units represented by the formulae (I-1), (I-2), (I-7), (I-8), (I-13) and (I-14) are more preferred, and structural units represented by the formulae (I-13) and (I-14) are particularly preferred. These may be included either alone or in combination of two or more thereof.

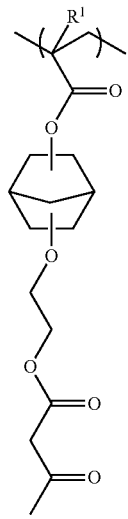

(1-1)

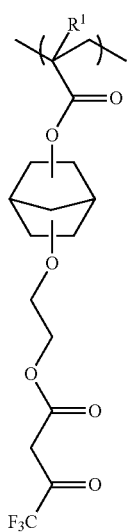

(1-2)

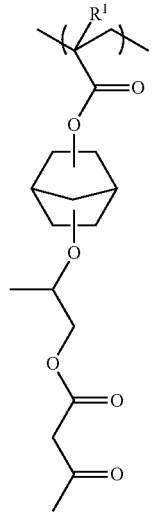

(1-3)

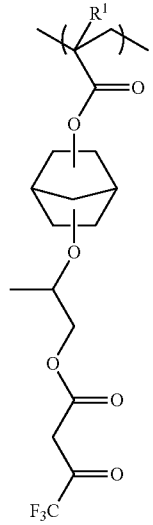

(1-4)

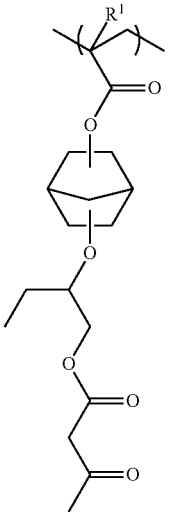

(1-5)

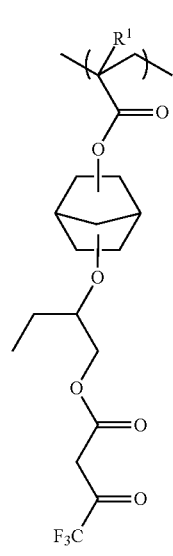 (1-6)
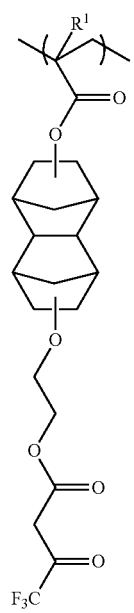 (1-8)
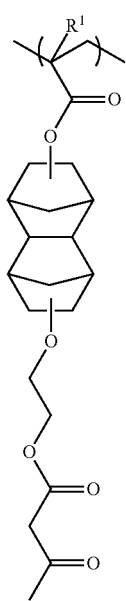 (1-7)
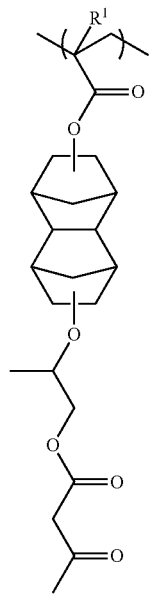 (1-9)

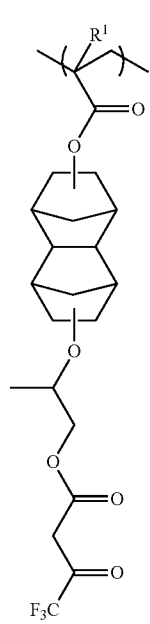 (1-10)
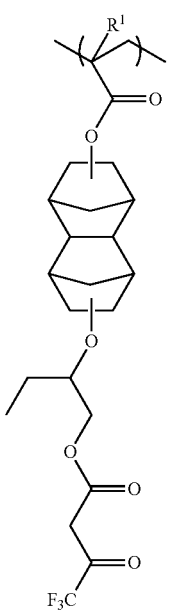 (1-12)
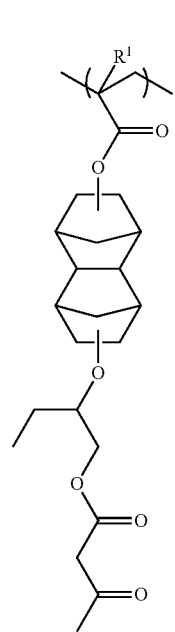 (1-11)
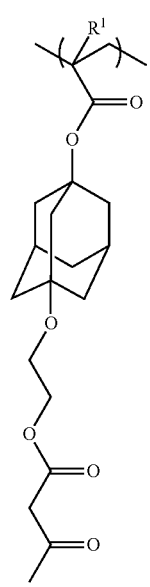 (1-13)

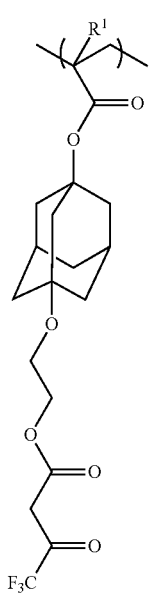 (1-14)
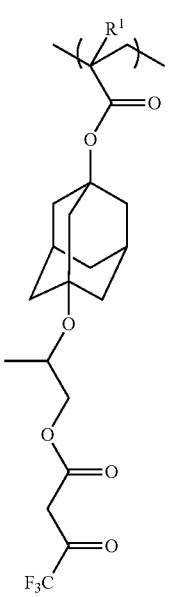 (1-16)
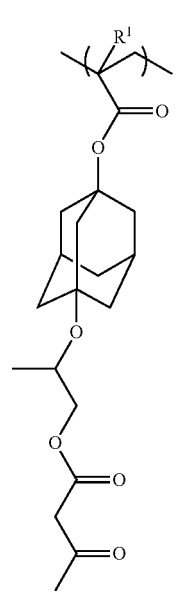 (1-15)
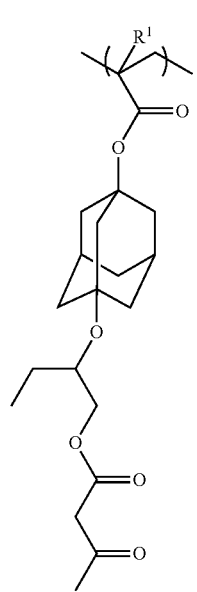 (1-17)

(1-18)

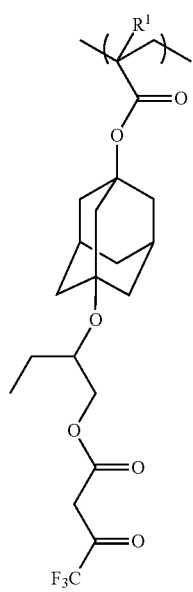

In the above formulae (1-1) to (1-18), $R^1$ is as defined in the above formula (I).

When the polymer (A1) is used, the proportion of the structural unit (1) contained with respect to entire structural units constituting the polymer (A) is preferably 1 mol % to 60 mol %, more preferably 1 mol % to 50 mol %, and particularly preferably 1 mol % to 40 mol %. On the other hand, when the polymer (A2) is used, the proportion of the structural unit (1) contained with respect to entire structural units constituting the polymer (A) is preferably 1 mol % to 90 mol %, more preferably 10 mol % to 80 mol %, and particularly preferably 20 mol % to 70 mol %. When the proportion of the structural unit (1) falls within the above range, the radiation-sensitive resin composition has highly balanced resist characteristics such as sensitivity, and LWR.

The compound (i) that gives the structural unit (1) can be synthesized by, for example, allowing an alcohol compound and a diketene derivative to react according to the following scheme. In the following scheme, according to pathway (a), the reaction is carried out usually using tetrahydrofuran, etc., as a solvent, triethylamine, etc., as a base, and dimethylaminopyridine, etc., as a catalyst. According to pathway (b) an ester exchange reaction is carried out usually using toluene, etc., as a solvent, and dimethylaminopyridine, etc., as a base. In this reaction, an acid may be used. After completion of the reaction, the intended compound can be obtained by subjecting to appropriate treatments such as analysis, washing, distillation and column chromatography. Also, according to pathway (c), one of hydroxyl groups of diol that has Y is allowed to react with 3,4-dihydro-2H-pyran, etc., in the presence of an acid catalyst to execute a protection. Subsequently, an exchange reaction with trifluoroethyl acetoacetate is carried out to further permit a deprotecting reaction, whereby the following alcohol 1 is obtained. On the other hand, sulfonic acid ester 1 is obtained by allowing an alcohol shown in the figure having X to react with an alkylsulfonyl chloride such as methylsulfonyl chloride. The product is allowed to react with the alcohol 1, whereby the intended compound is obtained.

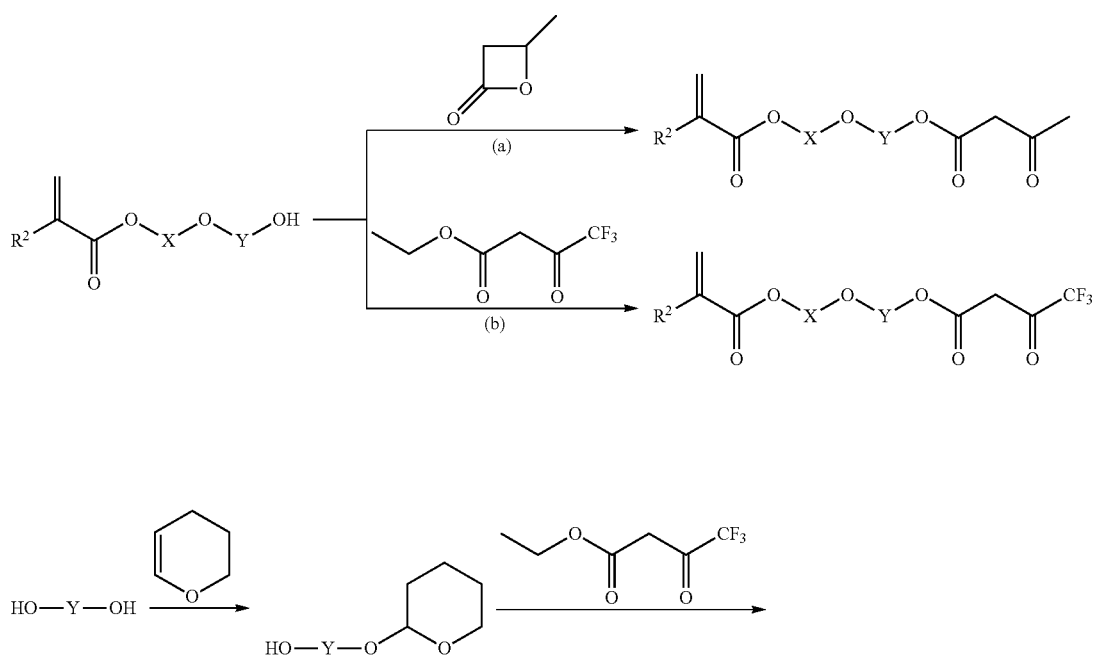

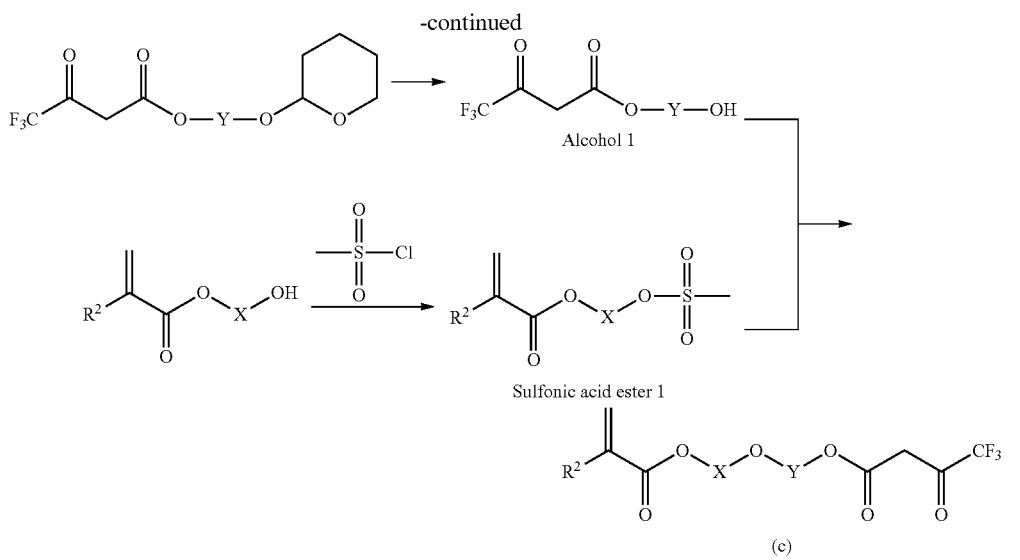

Alcohol 1

Sulfonic acid ester 1

(c)

In the above scheme, $R^1$, $R^2$, X and Y are as defined in the above formula (I).

Structural Unit (2)

The structural unit (2) is represented by the following formula (2). The structural unit (2) can be suitably used as a structural unit used for including an acid-dissociable group in the polymer (A1). The structural unit (2) has a group that generates a (meth)acrylate structure upon dissociation of —$CR^4R^5R^6$ in the presence of an acid, and incorporation of this structural unit leads to improvement of resolving performances as a resist of a radiation-sensitive resin composition containing the polymer (A1).

(2)

In the above formula (2), $R^3$ represents a hydrogen atom or a methyl group; $R^4$, $R^5$ and $R^6$ each independently represent an alkyl group having 1 to 4 carbon atoms or monovalent alicyclic hydrocarbon group having 4 to 20 carbon atoms, wherein $R^5$ and $R^6$ do not or optionally taken together represent bivalent alicyclic hydrocarbon group having 4 to 20 carbon atoms bivalent alicyclic hydrocarbon group having 4 to 20 carbon atoms together with the carbon atom to which they are attached.

Examples of the alkyl group having 1 to 4 carbon atoms include a methyl group, an ethyl group, a n-propyl group, a n-butyl group, and the like. Examples of the monovalent alicyclic hydrocarbon group having 4 to 20 carbon atoms include: monocyclic alicyclic hydrocarbon groups such as a cyclobutyl group, a cyclopentyl group, a cyclohexyl group and a cyclooctyl group; bridged alicyclic hydrocarbon groups such as a norbornyl group, a tricyclodecyl group, a tetracyclododecyl group and an adamantyl group, and the like.

Examples of the bivalent alicyclic hydrocarbon group having 4 to 20 carbon atoms include: monocyclic alicyclic hydrocarbon groups such as a cyclobutanediyl group, a cyclopentanediyl group, a cyclohexanediyl group and a cyclooctanediyl group; bridged alicyclic hydrocarbon groups such as a norbornanediyl group, a tricyclodecanediyl group, a tetracyclododecanediyl group and an adamantanediyl group, and the like.

The group represented by —$CR^4R^5R^6$ in the above formula (2) is exemplified by branched alkyl groups such as a tert-butyl group and a tert-amyl group; groups having an alicyclic structure represented by the following formula, and the like.

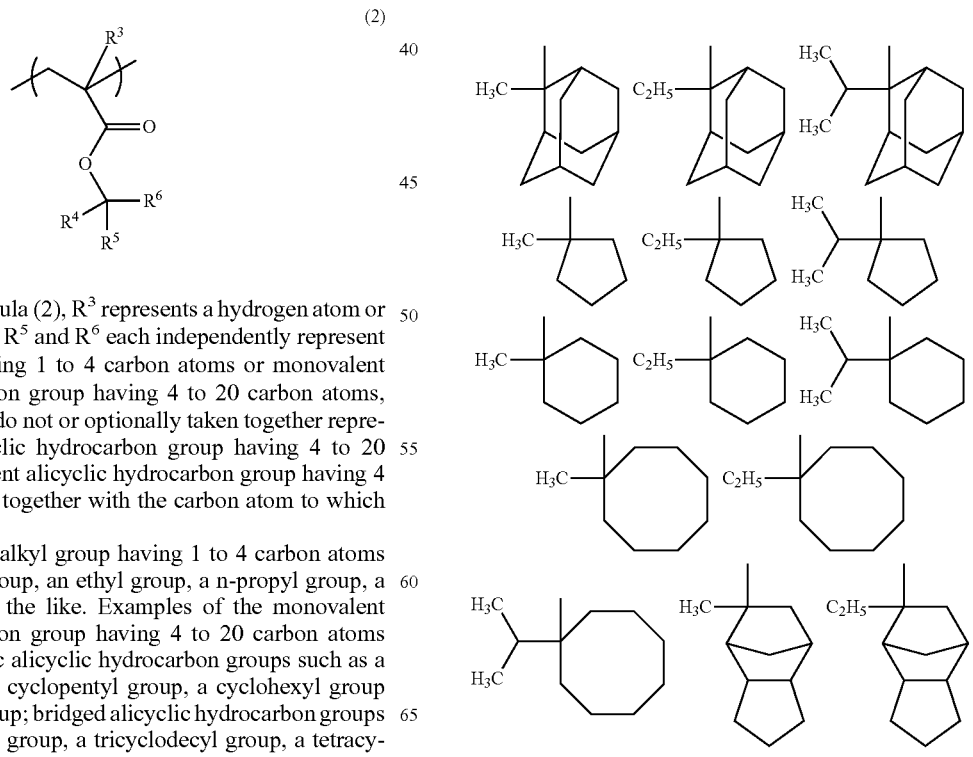

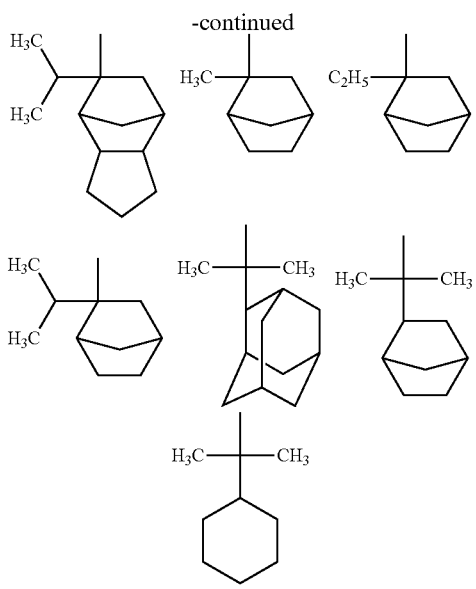
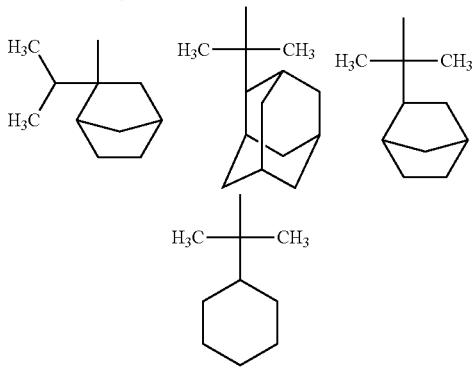
Examples of the structural unit (2) include structural units represented by the following formulae (2-1) to (2-20), and the like.
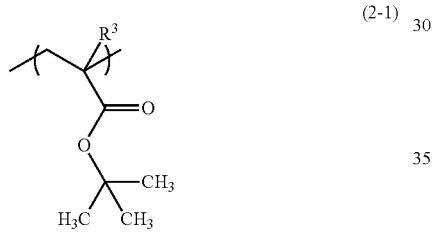 (2-1)
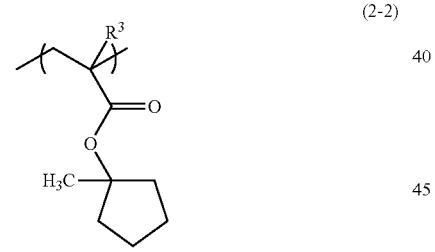 (2-2)
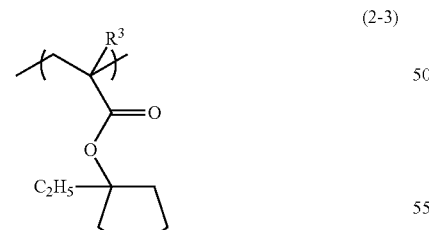 (2-3)
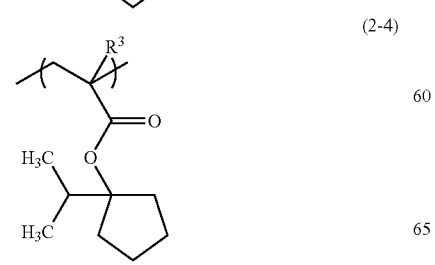 (2-4)
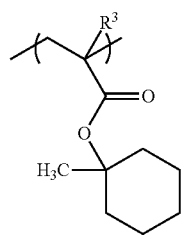 (2-5)
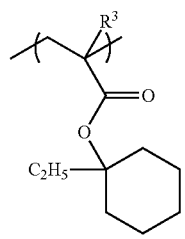 (2-6)
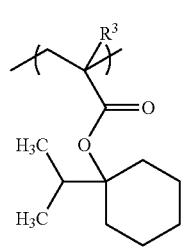 (2-7)
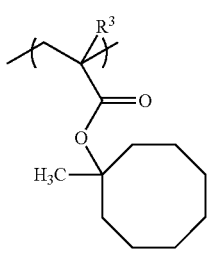 (2-8)
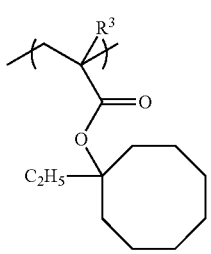 (2-9)
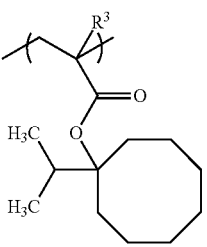 (2-10)

(2-11) 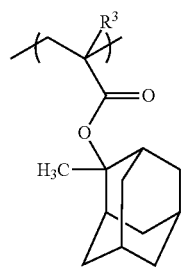
(2-12) 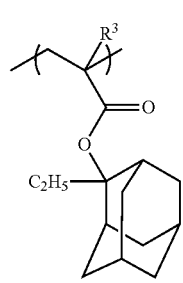
(2-13) 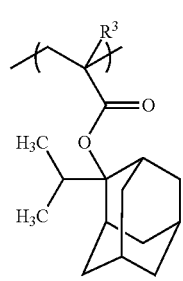
(2-14) 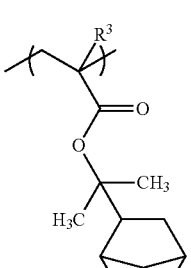
(2-15) 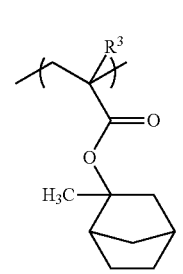
(2-16) 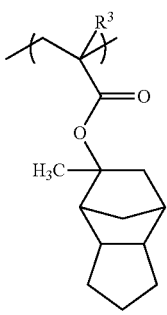
(2-17) 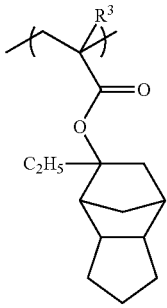
(2-18) 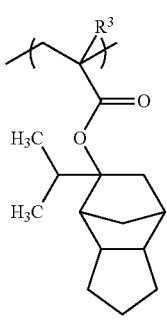
(2-19) 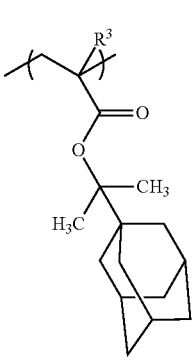
(2-20) 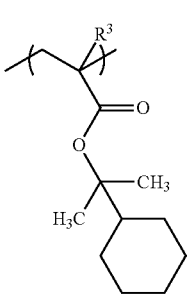
In the above formulae (2-1) to (2-20), $R^3$ is as defined in the above formula (2).

Of these, the structural units represented by the following formulae (2-1), (2-2), (2-3), (2-4), (2-5), (2-6), (2-8), (2-9), (2-11), (2-12), (2-13), (2-14) and (2-15) are preferred. These structural units may be included either alone, or in combination of two or more types thereof.

In the polymer (A1), the proportion of the structural unit (2) contained with respect to entire structural units constituting the polymer (A1) is preferably 5 mol % to 80 mol %, more preferably 10 mol % to 80 mol %, and particularly preferably 20 mol % to 70 mol %. When the proportion of the structural unit (2) contained falls within the above range, superior resolution and superior adhesiveness of the resist film can be attained, and pattern collapse and pattern peeling can be prevented.

Structural Unit (3)

The polymer (A) may further have, for example, at least one structural unit (3) selected from the group consisting of a structural unit that includes a lactone structure represented by the following formulae (III-1) to (III-5) and a structural unit having a cyclic carbonate structure represented by the following formula (III-6). In particular, it is preferred that the polymer (A1) has such a structural unit. When the polymer (A) further has the structural unit (3), the radiation-sensitive resin composition can exert resist characteristics with highly balanced sensitivity, resolution and exposure latitude, and exhibit a synergistic effect of improving developability, resistance to defects, low dependence on PEB temperature and the like as a resist.

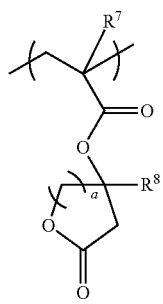

(III-1)

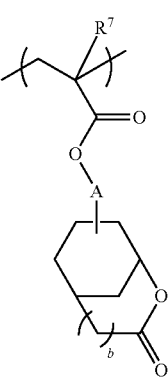

(III-2)

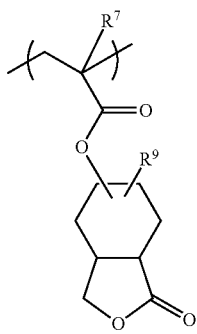

(III-3)

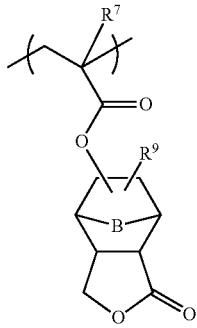

(III-4)

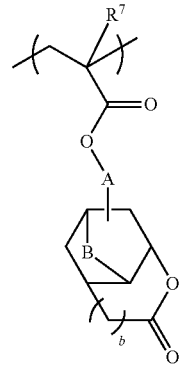

(III-5)

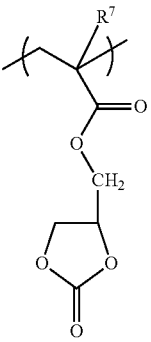

(III-6)

In the above formulae (III-1) to (III-6), $R^7$ and $R^8$ each independently represent a hydrogen atom or a methyl group; $R^9$ represents a hydrogen atom or a methoxy group; A represents a single bond or a methylene group; B represents a methylene group or an oxygen atom; a and b are each independently an integer of 0 to 2.

The structural unit (3) is preferably those represented by the following formulae (III-1a) to (III-6). These may be included either alone, or two or more types thereof may be included.

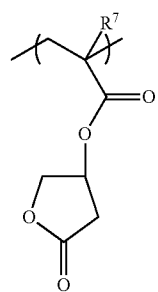
(III-1a)
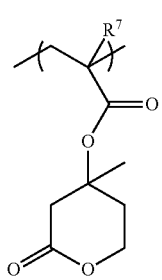
(III-1b)
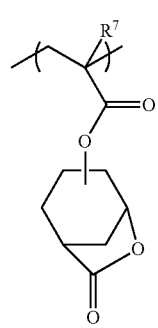
(III-2a)
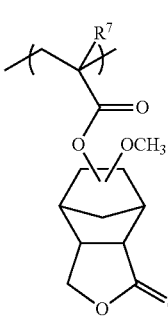
(III-3a)
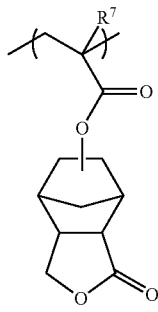
(III-4a)
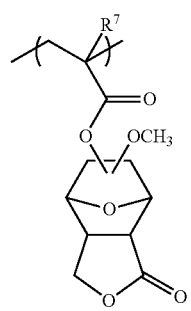
(III-4b)
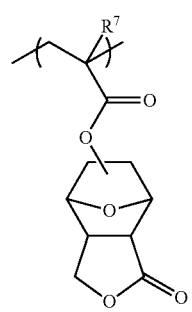
(III-4c)
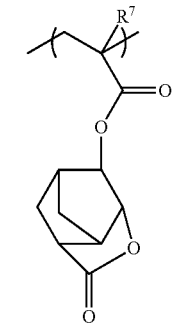
(III-5a)
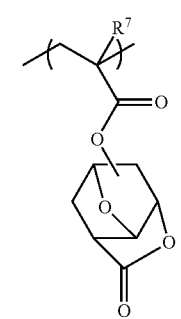
(III-5b)
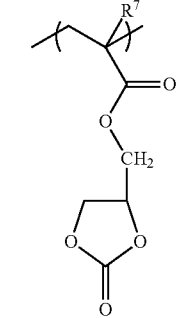
(III-6)

In the above formulae (III-1a) to (III-6), $R^7$ is as defined in the above formulae (III-1) to (III-6).

The proportion of the structural unit (3) contained with respect to entire structural units constituting the polymer (A) is preferably 0 mol % to 70 mol %, and more preferably 0 mol % to 60 mol %. When the proportion of the structural unit (3) contained falls within the above range, developability, resistance to defects, low dependence on PEB temperature and the like as a resist can be improved. It is to be noted that when the proportion of the structural unit (3) contained is greater than 70 mol %, the resolving ability as a resist may be deteriorated.

Other Structural Unit

The polymer (A) may further have as other structural unit except for the structural units (1) to (3), for example, at least one structural unit represented by any of the following formulae.

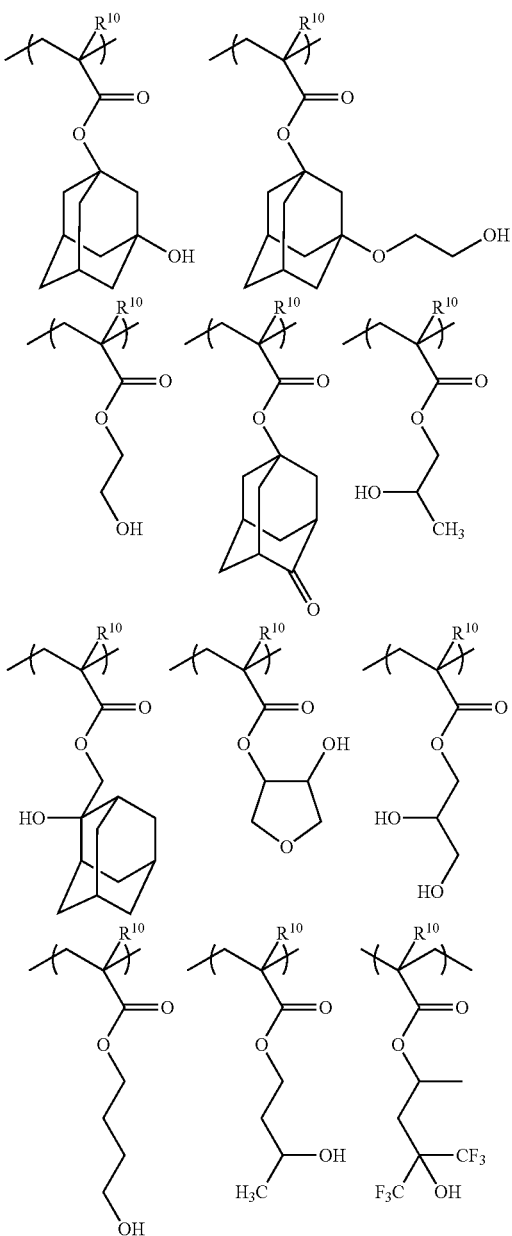

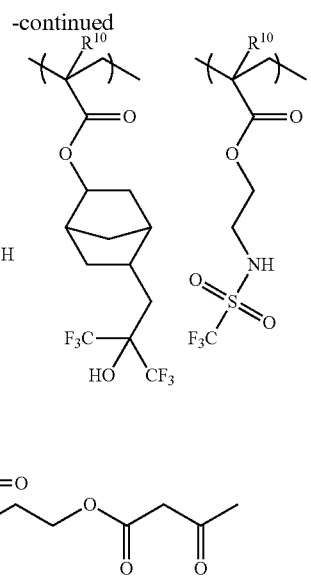

In the above formulae, $R^{10}$ represents a hydrogen atom or a methyl group;

In addition, the polymer (A) may further have a structural unit derived from, for example, an alkyl(meth)acrylate such as methyl(meth)acrylate, ethyl(meth)acrylate, n-butyl(meth)acrylate, lauryl(meth)acrylate, cyclohexyl(meth)acrylate, a (meth)acrylic acid bicyclo[2.2.1]heptyl ester, a (meth)acrylic acid cyclohexyl ester, a (meth)acrylic acid bicyclo[4.4.0]decanyl ester, a (meth)acrylic acid bicyclo[2.2.2]octyl ester, a (meth)acrylic acid tricyclo[5.2.1.0$^{2,6}$]decanyl ester, a (meth)acrylic acid adamantyl or a (meth)acrylic acid tricyclo[3.3.1.1$^{3,7}$]decanyl ester.

Synthesis Method of Polymer (A)

The polymer (A) may be synthesized according to a common procedure such as radical polymerization. The polymer (A) is preferably synthesized according to a method such as, e.g.:

a method in which a solution containing a monomer and a radical initiator is added dropwise to a solution containing a reaction solvent or a monomer to permit a polymerization reaction;

a method in which a solution containing a monomer, and a solution containing a radical initiator are each separately added dropwise to a solution containing a reaction solvent or a monomer to permit a polymerization reaction; or a method in which a plurality of solutions each containing a monomer, and a solution containing a radical initiator are each separately added dropwise to a solution containing a reaction solvent or a monomer to permit a polymerization reaction.

It is to be noted that when the reaction is allowed by adding a monomer solution dropwise to a monomer solution, the amount of the monomer in the monomer solution added is preferably no less than 30 mol %, more preferably no less than 50 mol %, and particularly preferably no less than 70 mol % with respect to the total amount of the monomers used in the polymerization.

The reaction temperature in these methods may be determined ad libitum depending of the type of the initiator species. The reaction temperature is usually 30° C. to 150° C., preferably 40° C. to 150° C., and more preferably 50° C. to 140° C. Time period for the dropwise addition may vary depending on the conditions such as the reaction temperature, the type of the initiator and the monomer to be reacted, but is usually 30 min to 8 hrs, preferably 45 min to 6 hrs, and more preferably 1 hour to 5 hrs. Further, the total reaction time period including time period for dropwise addition may also vary depending on the conditions similarly to the time period for the dropwise addition, and is usually 30 min to 12 hrs, preferably 45 min to 12 hrs, and more preferably 1 hour to 10 hrs.

The radical initiator for use in the polymerization is exemplified by azobisisobutyronitrile (AIBN), 2,2'-azobis(4-methoxy-2,4-dimethylvaleronitrile), 2,2'-azobis(2-cyclopropyl propionitrile), 2,2'-azobis(2,4-dimethylvaleronitrile), and the like. These radical initiators may be used either alone, or as a mixture of two or more thereof.

A reaction solvent used for the polymerization reaction is not limited as long as the solvent is one other than solvents that inhibit polymerization (i.e., nitrobenzene having a polymerization inhibitory effect, a mercapto compound having a chain transfer effect, and the like), and is capable of dissolving the monomer. Such a solvent is exemplified by an alcohol solvent, a ketone solvent, an amide solvent, an ester.lactone solvent, a nitrile solvent, a mixed solvent of these, and the like. These solvents may be used either alone, or in combination of two or more thereof.

The polymer obtained by the polymerization reaction may be recovered preferably by a reprecipitation technique. More specifically, after the polymerization reaction is completed, the polymerization reaction mixture is charged into a solvent for reprecipitation, whereby the intended polymer is recovered in the form of powder. As the reprecipitation solvent, an alcohol, an alkanes or the like may be used either alone or as a mixture of two or more thereof. Alternatively to the reprecipitation technique, liquid separating operation, column operation, ultrafiltration operation or the like may be employed to recover the polymer obtained by the polymerization reaction through eliminating low molecular components such as monomers and oligomers.

Although the polystyrene equivalent weight average molecular weight (Mw) of the polymer (A) as determined by gel permeation chromatography (GPC) is not particularly limited, is preferably no less than 1,000 and no greater than 100,000, more preferably no less than 1,000 and no greater than 300,000, and particularly preferably no less than 1,000 and no greater than 20,000. When the Mw of the polymer (A) is less than 1,000, heat resistance of the resulting resist is likely to be inferior. On the other hand, when the Mw of the polymer (A) exceeds 100,000, developability of the resulting resist is likely to be inferior.

In addition, a ratio (Mw/Mn) of the Mw to the polystyrene equivalent number average molecular weight (Mn) as determined by GPC of the polymer (A) is usually no less than 1.0 and no greater than 5.0, preferably no less than 1.0 and no greater than 3.0, and more preferably no less than 1.0 and no greater than 2.0. It is to be noted that the Mw and Mn as referred to herein means a value determined by GPC using GPC columns (manufactured by Tosoh Corporation, G2000HXL×2, G3000HXL×1, G4000HXL×1), under analysis conditions involving a flow rate of 1.0 milliliter/min, an elution solvent of tetrahydrofuran and a column temperature of 40° C. using mono-dispersed polystyrene as a standard.

(B) Acid Generator

The acid generator (B) is a component that generates an acid upon exposure. The acid-dissociable group existing in the polymer (A1) is dissociated by way of the acid generated, whereas the polymer (A2) is crosslinked by the crosslinking agent. As a result, solubility of the polymer (A) in a developer solution is altered. For example, the polymer (A1) becomes soluble in alkalis; therefore, light-exposed sites are dissolved in a developer solution to form a positive type pattern when an alkaline developer solution is used, whereas light-unexposed sites are dissolved in a developer solution to form a negative pattern when a developer solution of an organic solvent is used. It is to be noted that the form of the radiation-sensitive resin composition contained in the acid generator (B) may be in the form of either a compound as described later (hereinafter, may be referred to as appropriately "(B) acid generating agent") or a form incorporated as a part of the polymer (A) or other polymer, or may be in both of there forms.

Examples of the (B) acid generating agent include onium salt compounds, sulfonimide compounds, halogen-containing compound, diazoketone compounds, and the like. Among these (B) acid generators, onium salt compounds are preferred.

Examples of the onium salt compound include sulfonium salts, tetrahydrothiophenium salts, iodonium salts, phosphonium salts, diazonium salts, pyridinium salts, and the like. Of these onium salt compounds, sulfonium salts are preferred.

Examples of the sulfonium salt include triphenylsulfonium trifluoromethanesulfonate, triphenylsulfonium perfluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium camphorsulfonate, 4-cyclohexylphenyldiphenylsulfonium trifluoromethanesulfonate, 4-cyclohexylphenyldiphenylsulfonium perfluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium perfluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, and the like. Of these, triphenylsulfonium trifluoromethanesulfonate and triphenylsulfonium perfluoro-n-butanesulfonate are preferred, and triphenylsulfonium perfluoro-n-butanesulfonate is more preferred.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium perfluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(4-n-butoxynaphthalen-1-yl)tetrahydrothiopheniumcamphorsulfonate, 1-(6-n-butoxynaphthalen-2-yl)tetrahydrothiophenium trifluoromethanesulfonate, 1-(6-n-butoxynaphthalen-2-yl)tetrahydrothiophenium perfluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiopheniumcamphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium perperfluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiopheniumcamphorsulfonate, and the like. Of these tetrahydrothiophenium salts, 1-(4-n-butoxynaphthalen-1-yl)tetrahydrothiophenium perfluoro-n-butanesulfonate, 1-(4-n-butoxynaphthalen-1-yl)tetrahydrothiophenium perfluoro-n-octanesulfonate and 1-(3,5-dimethyl-4-hydroxyphenyl)tetrahydrothiophenium perfluoro-n-butanesulfonate are preferred.

Examples of the iodonium salt include diphenyliodonium trifluoromethanesulfonate, diphenyliodonium perfluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium perfluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like. Of these iodonium salts, bis(4-t-butylphenyl)iodonium perfluoro-n-butanesulfonate is preferred.

Examples of the sulfonimide compound include N-(trifluoromethanesulfonyloxy)bicyclo[2.2.1]hept-5-ene-2,3-dicarboxylmide, N-(perfluoro-n-butanesulfonyloxy)bicyclo[2.2.1]hept-5-ene-2,3-dicarboxylmide, N-(perfluoro-n-octanesulfonyloxy)bicyclo[2.2.1]hept-5-ene-2,3-dicarboxylmide, N-(2-bicyclo[2.2.1]hept-2-yl-1,1,2,2-tetrafluoroethanesulfonyloxy)bicyclo[2.2.1]hept-5-ene-2,3-dicarboxylmide, N-(2-(3-tetracyclo[$4.4.0.1^{2,5} \cdot 1^{7,10}$]dodecanyl)-1,1-difluoroethanesulfonyloxy)bicyclo[2.2.1]hept-5-ene-2,3-dicarboxylmide, N-(camphorsulfonyloxy)bicyclo[2.2.1]hept-5-ene-2,3-dicarboxylmide, and the like. Of these sulfonimide compounds, N-(trifluoromethanesulfonyloxy)bicyclo[2.2.1]hept-5-ene-2,3-dicarboxylmide is preferred.

The acid generator (B) may be used either alone or as a mixture of two or more thereof. The content of the acid generating agent (B) is in light of securement of sensitivity and developability as a resist, typically 0.1 parts by mass to 20 parts by mass, and preferably 0.5 parts by mass to 15 parts by mass with respect to 100 parts by mass of the polymer (A). In this case, when the content of the acid generating agent (B) is less than 0.1 parts by mass, sensitivity and developability tend to decrease, whereas when the content exceeds 10 parts by mass, radiation transmittance decreases, whereby obtaining a rectangular resist pattern tends to be difficult.

Optional Component

The radiation-sensitive resin composition may contain in addition to the foregoing polymer (A) and acid generator (B), a fluorine-containing resin, an alicyclic skeleton-containing compound, a surfactant, an acid diffusion controller, a crosslinking agent, an sensitizing agent, and the like as optional components within a range not leading to impairment of the effects of the present invention. The content of the optional component may be predetermined ad libitum to meet the intended object, and each of the optional component may be used wither alone or as a mixture of two or more thereof. These optional components will be described in detail below.

Fluorine-Containing Resin

The fluorine-containing resin has an effect of providing water repellency to the surface of the resist film particularly in liquid immersion lithography. Also, it exhibits an effect of inhibiting elution of components from the resist film to the liquid immersion liquid, and further droplets are prevented from remaining even if liquid immersion lithography is carried out by fast scanning; therefore, as a result, an effect of suppressing defects derived from liquid immersion such as water mark and the like is achieved.

The structure of the fluorine-containing resin may include:

a fluorine-containing resin which is insoluble in a developing solution per se and will be alkali soluble due to the action of an acid;

a fluorine-containing resin which is soluble in a developing solution per se and will have increased alkali solubility due to the action of an acid;

a fluorine-containing resin which is insoluble in a developing solution per se and will be alkali soluble due to the action of an alkali;

a fluorine-containing resin which is soluble in a developing solution per se and will have increased alkali solubility due to the action of an alkali; and the like.

The fluorine-containing resin is preferably a polymer having a fluorine-containing structural unit. Examples of a monomer that gives the fluorine-containing structural unit include a trifluoromethyl(meth)acrylic acid ester, a 2,2,2-trifluoroethyl(meth)acrylic acid ester, a perfluoroethyl(meth)acrylic acid ester, a perfluoro n-propyl(meth)acrylic acid ester, a perfluoro i-propyl(meth)acrylic acid ester, a perfluoro n-butyl(meth)acrylic acid ester, a perfluoro i-butyl(meth)acrylic acid ester, a perfluoro t-butyl(meth)acrylic acid ester, a 2-(1,1,1,3,3,3-hexafluoropropyl)(meth)acrylic acid ester, a 1-(2,2,3,3,4,4,5,5-octafluoropentyl)(meth)acrylic acid ester, a perfluorocyclohexylmethyl(meth)acrylic acid ester, a 1-(2,2,3,3,3-pentafluoropropyl)(meth)acrylic acid ester, a 1-(3,3,4,4,5,5,6,6,7,7,8,8,9,9,10,10,10-heptadecafluorodecyl)(meth)acrylic acid ester, a 1-(5-trifluoromethyl-3,3,4,4,5,6,6,6-octafluorohexyl)(meth)acrylic acid ester, and the like.

The fluorine-containing resin is preferably, a copolymer having, for example, the fluorine-containing structural unit, and the structural unit (2) and/or the structural unit (3) constituting the polymer (A).

Alicyclic Skeleton-Containing Compound

The alicyclic skeleton-containing compound exhibits effects of further improving dry etching resistance, pattern configuration, adhesiveness with the substrate, and the like.

Examples of the alicyclic skeleton-containing compound include:

adamantane derivatives such as 1-adamantanecarboxylate, 2-adamantanone and t-butyl 1-adamantanecarboxylate;

deoxycholic acid esters such as t-butyl deoxycholate, t-butoxycarbonylmethyl deoxycholate and 2-ethoxyethyl deoxycholate;

lithocholic acid esters such as t-butyl lithocholate, t-butoxycarbonylmethyl lithocholate and 2-ethoxyethyl lithocholate;

3-[2-hydroxy-2,2-bis(trifluoromethyl)ethyl]tetracyclo[$4.4.0.1^{2,5} \cdot 1^{7,10}$]dodecane, 2-hydroxy-9-methoxycarbonyl-5-oxo-4-oxa-tricyclo[$4.2.1.0^{3,7}$]nonane, and the like.

Surfactant

The surfactant has an effect of improving coating properties, striation, developability and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; as well as commercially available products such as KP341 (manufactured by Shin-Etsu Chemical Co., Ltd.), Polyflow No. 75 and Polyflow No. 95 (manufactured by Kyoeisha Chemical Co., Ltd.), EFTOP EF301, EFTOP EF303 and EFTOP EF352 (all manufactured by Tochem Products Corporation), Megaface® F171 and Megaface® F173 (all manufactured by Dainippon Ink And Chemicals, Incorporated), Fluorad™ FC430 and Fluorad™ FC431 (all manufactured by Sumitomo 3M Limited), ASAHI GUARD AG710, Surflon S-382, Surflon SC-101, Surflon SC-102, Surflon SC-103, Surflon SC-104, Surflon SC-105 and Surflon SC-106 (all manufactured by Asahi Glass Co., Ltd.), and the like.

Acid Diffusion Controller

The acid diffusion controller exhibits an effect of controlling a phenomenon of diffusion of an acid, which is generated from the acid generator (B) and the like upon exposure, in the resist coating film, and inhibiting an undesired chemical reaction in an unexposed region. In addition, the acid diffusion controller further improves the storage stability of the resulting radiation-sensitive resin composition and the resolution as a resist is further improved. Also, an alteration of line width of the resist pattern due to varying post-exposure delay (PED) from the exposure to the development process to be prevented so that a radiation-sensitive resin composition that exhibits excellent process stability can be obtained. The acid diffusion controller may be contained in the radiation-sensitive resin composition in a free compound form (hereinafter, appropriately referred to as "acid diffusion control agent") or in an incorporated form as a part of the polymer (A), or in both of these forms.

The acid diffusion control agent is exemplified by a nitrogen-containing compound having an acid-dissociable group represented by the following formula, etc., and the like.

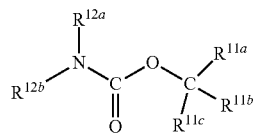

In the above formula, $R^{11a}$, $R^{11b}$, $R^{11c}$, $R^{12a}$ and $R^{12b}$ each independently represent a hydrogen atom, a linear, branched or cyclic alkyl group, an aryl group or an aralkyl group. Each of the hydrogen atom, the linear, branched or cyclic alkyl group, the aryl group and the aralkyl group has 1 to 20 carbon atoms. A part or all of hydrogen atoms included in these groups may be substituted. In addition, a plurality of $R^{11}$s or a plurality of $R^{12}$s may taken together represent a ring structure having 4 to 20 carbon atoms together with the carbon atom or the nitrogen atom to which they bond.

Examples of the nitrogen-containing compound having an acid-dissociable group include N-t-alkylalkoxycarbonyl group-containing amino compounds such as N-t-butoxycarbonyl di-n-octylamine, N-t-butoxycarbonyl di-n-nonylamine, N-t-butoxycarbonyl di-n-decylamine, N-t-butoxycarbonyl dicyclohexylamine, N-t-butoxycarbonyl-1-adamantylamine, N-t-butoxycarbonyl-2-adamantylamine, N-t-butoxycarbonyl-N-methyl-1-adamantylamine, (S)-(−)-1-(t-butoxycarbonyl)-2-pyrrolidinemethanol, (R)-(+)-1-(t-butoxycarbonyl)-2-pyrrolidinemethanol, N-t-butoxycarbonyl-4-hydroxypiperidine, N-t-amyloxycarbonyl-4-hydroxypiperidine, N-t-butoxycarbonylpyrrolidine, N,N'-di-t-butoxycarbonylpiperazine, N,N-di-t-butoxycarbonyl-1-adamantylamine, N-t-butoxycarbonyl-4,4'-diaminodiphenylmethane, N,N'-di-t-butoxycarbonylhexamethylenediamine, N,N,N',N'-tetra-t-butoxycarbonylhexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole and N-t-butoxycarbonyl-2-phenylbenzimidazole, and the like.

Furthermore, the acid diffusion control agent is exemplified by a tertiary amine compound, a quaternary ammonium hydroxide compound, a photodegradable base compound, other nitrogen-containing heterocyclic compound, and the like in addition to the nitrogen-containing compound having an acid-dissociable group described above.

Examples of the tertiary amine compound include tri(cyclo)alkylamines such as triethylamine, tri-n-propylamine, tri-n-butylamine, tri-n-pentylamine, tri-n-hexylamine, tri-n-heptylamine, tri-n-octylamine, cyclohexyl dimethylamine, dicyclohexylmethylamine and tricyclohexylamine;

aromatic amines such as aniline, N-methylaniline, N,N-dimethylaniline, 2-methylaniline, 3-methylaniline, 4-s methylaniline, 4-nitroaniline, 2,6-dimethylaniline and 2,6-diisopropylaniline;

alkanolamines such as triethanolamine and N,N-di(hydroxyethyl)aniline;

N,N,N',N'-tetramethylethylenediamine, N,N,N',N'-tetrakis(2-hydroxypropyl)ethylenediamine, 1,3-bis[1-(4-aminophenyl)-1-methylethyl]benzenetetramethylenediamine, bis(2-dimethylaminoethyl)ether, bis(2-diethylaminoethyl)ether, and the like.

Examples of the quaternary ammonium hydroxide compound include tetra-n-propylammonium hydroxide, tetra-n-butylammonium hydroxide, and the like.

The content of the acid diffusion control agent with respect to 100 parts by mass of the total polymer in the radiation-sensitive resin composition is preferably less than 5 parts by mass, and more preferably less than 1 part by mass. When the total content exceeds 5 parts by mass, sensitivity as a resist is likely to be markedly deteriorated.

Crosslinking Agent

When the radiation-sensitive composition according to an embodiment of the present invention contains the polymer (A2), and forms a negative pattern upon development with an alkali, it is preferred that a crosslinking agent is further contained. More specifically, due to containing a crosslinking agent, a crosslinking reaction of the crosslinking agent proceeds in the radiation-sensitive resin composition by an action of an acid generated upon exposure, and crosslinking occurs between molecules of the polymer (A2) with one another and in the same molecule, whereby a crosslinked polymer having poor solubility in an alkaline developer solution is formed.

Such a crosslinking agent is not particularly limited as long as it enables the polymer (A2) to be crosslinked and the crosslinked polymer will be insoluble in an alkaline developer solution. The crosslinking agent is exemplified by compounds having a crosslinkable functional group, and the like. Examples of the crosslinkable functional group include groups having an epoxy group such as a glycidyl ether group, a glycidyl ester group or a glycidylamino group; a methoxymethyl group, an ethoxymethyl group, a benzyloxymethyl group, an acetoxymethyl group, a benzoyloxymethyl group, a formyl group, an acetyl group, a vinyl group, an isopropenyl group, a dimethylaminomethyl group, a diethylaminomethyl group, a dimethylolaminomethyl group, a diethylolaminomethyl group, a morpholinomethyl group, and the like.

Examples of the compound having a crosslinkable functional group include bisphenol A type epoxy compounds, bisphenol F type epoxy compounds, bisphenol S type epoxy compounds, novolak resin type epoxy compounds, resol resin type epoxy compounds, poly(hydroxystyrene) type epoxy compounds, methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compounds, alkoxyalkyl group-containing phenol compounds, carboxylmethyl group-containing melamine resins, carboxylmethyl group-containing benzoguanamine resins, carboxylmethyl group-containing urea resins, carboxylmethyl group-containing phenol resins, carboxylmethyl group-containing melamine compounds, carboxylmethyl group-containing benzoguanamine compounds, carboxylmethyl group-containing urea compounds, carboxylmethyl group-containing phenol compounds, and the like.

Of these compounds having a crosslinkable functional group, methylol group-containing phenol compounds, methoxymethyl group-containing melamine compounds, methoxymethyl group-containing phenol compounds, methoxymethyl group-containing glycol uril compounds, methoxymethyl group-containing urea compounds and acetoxymethyl group-containing phenol compounds are preferred; methoxymethyl group-containing melamine compounds such as hexamethoxymethylmelamine, methoxymethyl group-containing glycol uril compounds and methoxymethyl group-containing urea compounds are further preferred; and 1,3-bis(methoxymethyl)urea and 1,3,4,6-tetrakis(methoxymethyl)glycol uril are particularly preferred.

Sensitizing Agent

The sensitizing agent serves in absorbing the energy other than the energy of radioactive rays absorbed by the acid generator (B), and transferring the energy to the acid generator (B) in the form of, for example, a radical, thereby increasing the amount of acid generation, and thus exerts an effect of improving "apparent sensitivity" of the radiation-sensitive resin composition.

Examples of the sensitizing agent include carbazoles, acetophenones, benzophenones, naphthalenes, phenols, biacetyl, eosin, rose bengal, pyrenes, anthracenes, phenothiazines, and the like.

Other Optional Components

The other optional components are exemplified by a dye, a pigment, an adhesion promoter, an alkali-soluble resin, a low molecular alkali-soluble control agent having an acid dissociable protecting group, an halation inhibitor, a storage stabilizing agent, a defoaming agent, and the like. Of these, when, for example, a dye or a pigment is blended, latent image at a light-exposed site can be visualized, and influences from halation upon exposure can be alleviated. In addition, when an adhesion promoter is blended, adhesiveness with a substrate can be improved.

Preparation Method of Radiation-Sensitive Resin Composition

The radiation-sensitive resin composition can be prepared as a positive or negative type radiation-sensitive resin composition by mixing, for example, the polymer (A), the acid generator (B), and the optional component(s) at a certain ratio in an organic solvent. The organic solvent is not particularly limited as long as it can dissolve the polymer (A), the acid generator (B) and the optional component(s). The organic solvent is exemplified by an alcohol solvent, a ketone solvent, an amide solvent, an ether solvent, an ester solvent, a hydrocarbon solvent, a halogenated hydrocarbon solvent, a mixed solvent of the same, and the like.

Examples of the alcohol solvent include:

monohydric alcohol solvents such as methanol, ethanol, n-propanol, i-propanol, n-butanol, i-butanol, sec-butanol, tert-butanol, n-pentanol, i-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

partially etherified polyhydric alcohol solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether; and the like.

Examples of the ketone solvent include ketone solvents such as acetone, methyl ethyl ketone, methyl n-propyl ketone, methyl n-butyl ketone, diethyl ketone, methyl isobutyl ketone, methyl n-pentyl ketone, ethyl-n-butyl ketone, methyl n-hexyl ketone, di-isobutyl ketone, trimethylnonanone, cyclopentanone, cyclohexanone, cycloheptanone, cyclooctanone, methylcyclohexanone, 2,4-pentanedione, acetonylacetone, diacetone alcohol and acetophenone.

Examples of the amide solvent include N,N'-dimethylimidazolidinone, N-methylformamide, N,N-dimethylformamide, N,N-diethylformamide, acetamide, N-methylacetamide, N,N-dimethylacetamide, N-methylpropionamide, N-methylpyrrolidone, and the like.

Examples of the ester solvent include diethyl carbonate, propylene carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, isoamyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the hydrocarbon solvent include:

aliphatic hydrocarbon solvents such as n-pentane, isopentane, n-hexane, isohexane, n-heptane, isoheptane, 2,2,4-trimethyl pentane, n-octane, isooctane, cyclohexane, and methylcyclohexane;

aromatic hydrocarbon solvents such as benzene, toluene, xylene, mesitylene, ethylbenzene, trimethylbenzene, methylethylbenzene, n-propylbenzene, isopropylbenzene, diethylbenzene, isobutylbenzene, triethylbenzene, di-isopropylbenzene, and n-amylnaphthalene; and the like.

Examples of the halogenated hydrocarbon solvent include:

halogen-containing aliphatic hydrocarbon solvents such as dichloromethane, chloroform and chlorofluorocarbon; chlorobenzene; halogen-containing aromatic hydrocarbon solvents such as dichlorobenzene, and the like.

Of these solvents, propylene glycol monomethyl ether acetate, cyclohexanone and γ-butyrolactone are preferred. These solvents may be used either alone or in combination of two or more types thereof.

Photoresist Pattern-Forming Method

Typical photoresist pattern-forming method is exemplified by the method shown in the following. A photoresist pattern can be formed by a method including: step (i) of providing a photoresist film on a substrate using the radiation-sensitive resin composition; step (ii) of exposing the provided photoresist film by irradiating with a radioactive ray through a mask having a predetermined pattern, via a liquid immersion medium as needed; step (iii) of heating the exposed photoresist film; and step (iv) of development. Each step will be described in detail below.

In the step (i), the radiation-sensitive resin composition is coated on a substrate such as a silicon wafer, a wafer coated with silicon dioxide or an antireflection film, or the like by an appropriate coating means such as spin-coating, cast coating or roll coating, followed by prebaking (PB) to allow a solvent in the coated film to be volatilized, whereby a photoresist film is provided.

In the case in which liquid immersion lithography is carried out, a protective film for liquid immersion that is insoluble in a liquid immersion liquid may be provided on the resist film prior to the step (ii) in order to protect the resist film from direct contact with the liquid immersion. As a protective film for liquid immersion, any one of a solvent-peelable protective film that is peeled by a solvent prior to the step (iv) described later (for example, see Japanese Unexamined Patent Application, Publication No. 2006-227632), and a developer solution-peelable protective film that is peeled concomitant with development in the step (iv) (see, for example, WO2005-069076 and WO2006-035790) may be used. However, in this step, a developer solution-peelable protective film for liquid immersion is preferably used in light of throughput.

In the step (ii), the photoresist film formed in the step (i) is exposed by irradiating with a radioactive ray (via a liquid immersion medium such as water as needed). In this step, the radioactive ray is irradiated through a mask having a predetermined pattern. The radioactive ray appropriately selected from visible light rays, ultraviolet rays, far ultraviolet rays, X-ray, charged particle ray and the like in accordance with the line width of the intended pattern may be irradiated. Of these, far ultraviolet rays are preferred; an ArF excimer laser beam (wavelength: 193 nm) and a KrF excimer laser beam (wavelength: 248 nm) are more preferred; and in particular, an ArF excimer laser beam is preferred.

The step (iii) is referred to as "post exposure baking (PEB)", in which the acid generated from the acid generator (B) deprotects the acid-dissociable group and the like included in the polymer at sites of the photoresist film exposed in the step (ii). PEB is performed at an appropriately selected temperature from the range of usually 50° C. to 180° C.

In the step (iv), the exposed photoresist film is developed with a developing solution to form a predetermined photoresist pattern. After the development, the film is, in general, washed with water, and then dried. The developing solution is preferably an alkali aqueous solution prepared by dissolving at least one of alkaline compounds such as, for example, sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene.

The resist pattern obtained in this manner has a small LWR value, and is accompanied by fewer defects. Therefore, the embodiment is suited for microfabrication in which a lithography technique is employed.

Polymer

The polymer according to an embodiment of the present invention has the structural unit represented by the above formula (I). The polymer can be suitably used in, for example, radiation-sensitive resin compositions and the like for use in lithography techniques. The explanation of details of the polymer is omitted here since the explanation was made in the section of explanation of the polymer (A) contained in the radiation-sensitive resin composition.

Compound

The compound according to an embodiment of the present invention is represented by the above formula (I). The explanation of details of the compound is omitted here since the explanation was made in the section of explanation of the polymer (A) contained in the radiation-sensitive resin composition.

EXAMPLES

Hereinafter, the present invention will be described in detail by way of Examples, but the present invention should not be construed as being limited to the Examples. Note that a $^{13}$C-NMR analysis carried out using a nuclear magnetic resonance apparatus (JNM-ECX400, manufactured by JEOL, Ltd.).

Synthesis of Compound Represented by the Above Formula (i)

Example 1

Into a 500 mL three-neck flask equipped with a thermometer and a reflux condenser, 20.0 g (71.3 mmol) of methacrylic acid-3-(2-hydroxyethoxy)-1-adamantyl, 4.0 mg (0.033 mmol) of N,N-dimethyl-4-aminopyridine, 36.1 mg (0.36 mmol) of triethylamine, 20 mg of phenothiazine and 100 mL of tetrahydrofuran (THF) were placed, and the mixture was stirred at 0° C. for 15 min. Subsequently, 6.59 g (78.4 mmol) of diketene dissolved in 50 mL of tetrahydrofuran was added dropwise over 15 min using a dropping funnel. After the dropwise addition, the mixture was further stirred at 0° C. for hrs, and then 5 mL of water was added to allow for quenching, thereby completing the reaction. Next, the reaction liquid was poured into a separatory funnel, and 300 mL of 2-butanone was further added thereto. This reaction liquid was washed with 100 mL of water twice and then with 100 mL of saturated saline once, and thereafter an oil layer was recovered and dried over anhydrous magnesium sulfate. After filtration of the solution, the solvent was vacuum distilled to obtain a compound (i-1) represented by the following formula (25.15 g; yield: 97%).

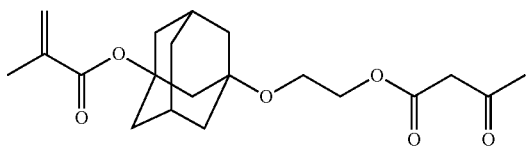

(i-1)

$^1$H-NMR (CDCl$_3$) δ: 6.00 (1H), 5.50 (1H), 4.25 (2H), 3.66 (2H), 3.48 (2H), 2.40-1.45 (20H)

Example 2

Into a flask equipped with a dropping funnel, 27.67 g of ethylene glycol, 0.57 g of paratoluenesulfonate monohydrate and 200 mL of dichloromethane were placed, and the mixture was stirred in an ice bath for 15 min. Thereto 25.00 g of 3,4-dihydro-2H-pyran dissolved in 30 mL of dichloromethane was added dropwise over 15 min. After completion of the dropwise addition, the mixture was further stirred in an ice bath for 15 min, followed by additional stirring at room temperature for 90 min. Thereafter, 50 mL of a saturated aqueous sodium bicarbonate solution was added, thereby completing the reaction. The reaction liquid was washed with 50 mL of water twice and then with 50 mL of saturated saline once, and thereafter an oil layer was recovered. Low-boiling point components were vacuum distilled to obtain a crude product. The crude product was purified on silica gel column chromatography to obtain a compound represented by the following formula (a1).

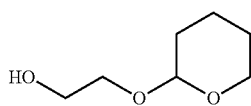

(a1)

Into a 1,000 mL three-neck flask equipped with a thermometer and a reflux condenser, 17.88 g of the compound represented by the above formula (a1), 15.00 g of trifluoroethyl acetoacetate, 9.96 g of N,N-dimethylaminopyridine and 600 mL of toluene were placed, and the temperature of the mixture was elevated to 110° C. with stirring, followed by stirring the mixture for 3 hrs while distilling off low-boiling point components. Thereafter, the mixture was cooled to room temperature, and the reaction liquid was washed with 100 mL of a 1 M aqueous hydrochloric acid solution three times and then with 100 mL of saturated saline once. Thereafter, the oil layer was recovered and low-boiling point components were vacuum distilled to obtain a crude product. The crude product was purified on silica gel column chromatography to obtain a compound represented by the following formula (a2).

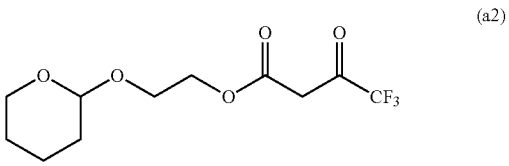 [SMILES: O=C(CC(=O)C(F)(F)F)OCCOC1CCCCO1]

(a2)

Into a 1,000 mL flask, 20.00 g of the compound represented by the above formula (a2), 0.27 g of toluenesulfonate monohydrate and 300 mL of methanol were placed, and the mixture was stirred at room temperature for 3 hrs. After stirring, low-boiling point components were vacuum distilled to obtain a crude product of a compound represented by the following formula (a3). In this procedure, the crude product was subjected to the following reaction without carrying out purification.

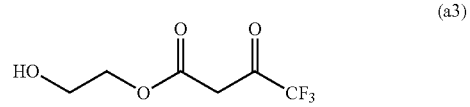 [SMILES: O=C(CC(=O)C(F)(F)F)OCCO]

(a3)

Into a 500 mL three-neck flask equipped with a thermometer and a dropping funnel, 11.00 g of the compound represented by the above formula (a3), 8.34 g of triethylamine and 300 mL of THF were placed, and the mixture was stirred in an ice bath for 15 min. Thereto was added 20.75 g of hydroxyadamantyl methacrylate methylsulfonyl ester dissolved in 30 mL of THF dropwise over 15 min. After the dropwise addition, the mixture was further stirred for 30 min in an ice bath, and then stirred at room temperature for 2 hrs. Then 5 mL of a 1 M aqueous hydrochloric acid solution was added, thereby completing the reaction. After completion of the reaction, THF was vacuum distilled, and 300 mL of ethyl acetate was added thereto. This solution was washed with 50 mL of a 1 M aqueous hydrochloric acid solution three times and then with 50 mL of saturated saline once, and thereafter an oil layer was recovered. A crude product was purified on silica gel column chromatography to obtain a compound represented by the following formula (I-2).

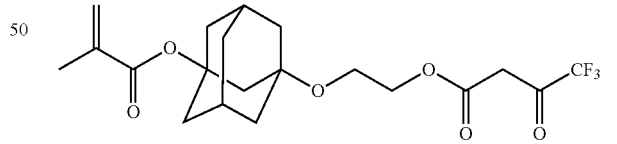

(i-2)

Synthesis of Polymer (A)

Monomers (M-1) to (M-5) used in the synthesis of the polymers (A-1), (A-2) and (CA-1) to (CA-3) are shown below.

(M-1): 2-methyl-2-adamantyl(meth)acrylate (M-2): 1-methyl-1-cyclopentyl(meth)acrylate (M-3) and (M-4): monomers represented by the following formulae

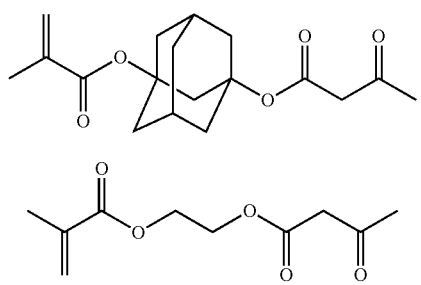

(M-3)

(M-4)

(M-5): 4-oxa-5-oxotricyclo[4,2,1,0^{3,7}]nonan-2-yl(meth)acrylate

It is to be noted that: the monomer (M-3) gives the structural unit (1); the monomers (M-1) and (M-2) give the structural unit (2); and the monomer (M-5) gives the structural unit (3), respectively, of the polymer (A).

Example 3

A monomer solution was prepared by dissolving 8.43 g (10 mol %) of the compound (i-1), 5.42 g (10 mol %) of the monomer (M-1), 15.57 g (40 mol %) of the monomer (M-2) and 20.57 g (40 mol %) of the monomer (M-5) in 100 g of 2-butanone, and further dissolving 1.90 g of AIBN as a polymerization initiator. Then, into a 500 mL three-neck flask equipped with a thermometer and a dropping funnel was placed 50 g of 2-butanone, and nitrogen was purged for 30 min. After purging with nitrogen, the content inside the flask was heated to 80° C. while stirring with a magnetic stirrer. The monomer solution prepared above was added dropwise via a dropping funnel over 3 hrs. The time of the start of the dropwise addition was considered to be the time of the initiation of the polymerization, and the polymerization reaction was allowed to proceed for 6 hrs. After completing the polymerization, the polymerization solution was cooled to no greater than 30° C. via water-cooling. After cooling, the polymerization solution was charged into a mixed solution of 800 g of methanol and 200 g of water, and a white powder precipitated was filtered off. The filtered white powder was washed twice by slurrying in 200 g of methanol. Thereafter, filtration and drying at 60° C. for 17 hrs gave the polymer (A-1) as a white powder (37.6 g; yield: 75%; Mw: 6,400; Mw/Mn: 1.51). The result of $^{13}$C-NMR analysis indicated that the ratio of the structural unit derived from the compound (i-1):the structural unit derived from the monomer (M-1):the structural unit derived from the monomer (M-2):the structural unit derived from the monomer (M-5) was 10.5:9.7:38.9:40.9 (mol %).

Example 4

A monomer solution was prepared by dissolving 9.45 g (10 mol %) of the compound (i-2), 5.29 g (10 mol %) of the monomer (M-1), 15.19 g (40 mol %) of the monomer (M-2) and 20.07 g (40 mol %) of the monomer (M-5) in 100 g of 2-butanone, and further dissolving 1.85 g of AIBN as a polymerization initiator. Then, into a 500 mL three-neck flask equipped with a thermometer and a dropping funnel was placed 50 g of 2-butanone, and nitrogen was purged for 30 min. After purging with nitrogen, the content inside the flask was heated to 80° C. while stirring with a magnetic stirrer. The monomer solution prepared above was added dropwise via a dropping funnel over 3 hrs. The time of the start of the dropwise addition was considered to be the time of the initiation of the polymerization, and the polymerization reaction was allowed to proceed for 6 hrs. After completing the polymerization, the polymerization solution was cooled to no greater than 30° C. via water-cooling. After cooling, the polymerization solution was charged into a mixed solution of 800 g of methanol and 200 g of water, and a white powder precipitated was filtered off. The filtered white powder was washed twice by slurrying in 200 g of methanol. Thereafter, filtration and drying at 60° C. for 17 hrs gave the polymer (A-2) as a white powder (34.8 g; yield: 70%; Mw: 6,800; Mw/Mn: 1.50). The result of $^{13}$C-NMR analysis indicated that the ratio of the structural unit derived from the compound (i-2):the structural unit derived from the monomer (M-1):the structural unit derived from the monomer (M-2):the structural unit derived from the monomer (M-5) was 10.0:9.1:39.1:41.8 (mol %).

Synthesis Example 1

A monomer solution was prepared by dissolving 5.54 g (10 mol %) of the monomer (M-1), 15.90 g (40 mol %) of the monomer (M-2), 7.57 g (40 mol %) of the monomer (M-3) and 21.00 g (40 mol %) of the monomer (M-5) in 100 g of 2-butanone, and further dissolving 1.94 g of AIBN as a polymerization initiator. Then, into a 500 mL three-neck flask equipped with a thermometer and a dropping funnel was placed 50 g of 2-butanone, and nitrogen was purged for 30 min. After purging with nitrogen, the content inside the flask was heated to 80° C. while stirring with a magnetic stirrer. The monomer solution prepared above was added dropwise via a dropping funnel over 3 hrs. The time of the start of the dropwise addition was considered to be the time of the initiation of the polymerization, and the polymerization reaction was allowed to proceed for 6 hrs. After completing the polymerization, the polymerization solution was cooled to no greater than 30° C. via water-cooling. After cooling, the polymerization solution was charged into a mixed solution of 800 g of methanol and 200 g of water, and a white powder precipitated was filtered off. The filtered white powder was washed twice in a slurry form with 200 g of methanol. Thereafter, filtration and drying at 60° C. for 17 hrs gave the polymer (CA-1) as a white powder (36.4 g; yield: 73%; Mw: 6,700; Mw/Mn: 1.52). The result of $^{13}$C-NMR analysis indicated that the ratio of the structural unit derived from the monomer (M-1):the structural unit derived from the monomer (M-2):the structural unit derived from the monomer (M-3):the structural unit derived from the monomer (M-5) was 9.9:38.5:10.8:40.8 (mol %).

Synthesis Example 2

A monomer solution was prepared by dissolving 5.83 g (10 mol %) of the monomer (M-1), 16.74 g (40 mol %) of the monomer (M-2), 5.33 g (40 mol %) of the monomer (M-4) and 22.11 g (40 mol %) of the monomer (M-5) in 100 g of 2-butanone, and further dissolving 2.04 g of AIBN as a polymerization initiator. Then, into a 500 mL three-neck flask equipped with a thermometer and a dropping funnel was placed 50 g of 2-butanone, and nitrogen was purged for 30 min. After purging with nitrogen, the content inside the flask was heated to 80° C. while stirring with a magnetic stirrer. The monomer solution prepared above was added dropwise via a dropping funnel over 3 hrs. The time of the start of the dropwise addition was considered to be the time of the initiation of the polymerization, and the polymerization reaction was allowed to proceed for 6 hrs. After completing the polymerization, the polymerization solution was cooled to no greater than 30° C. via water-cooling. After cooling, the polymerization solution was charged into a mixed solution of 800 g of methanol and 200 g of water, and a white powder precipitated was filtered off. The filtered white powder was washed twice in a slurry form with 200 g of methanol. Thereafter, filtration and drying at 60° C. for 17 hrs gave the polymer (CA-2) as a white powder (35.1 g; yield: 70%; Mw: 6,900; Mw/Mn: 1.50). The result of $^{13}$C-NMR analysis indicated that the ratio of the structural unit derived from the monomer (M-1):the structural unit derived from the monomer (M-2):the structural unit derived from the monomer (M-4):the structural unit derived from the monomer (M-5) was 9.8:39.1:10.5:40.6 (mol %).

Synthesis Example 3

A monomer solution was prepared by dissolving 5.80 g (10 mol %) of the monomer (M-1), 16.67 g (40 mol %) of the monomer (M-2) and 27.53 g (50 mol %) of the monomer (M-5) in 100 g of 2-butanone, and further dissolving 2.03 g of AIBN as a polymerization initiator. Then, into a 500 mL three-neck flask equipped with a thermometer and a dropping funnel was placed 50 g of 2-butanone, and nitrogen was purged for 30 min. After purging with nitrogen, the content inside the flask was heated to 80° C. while stirring with a magnetic stirrer. The monomer solution prepared above was added dropwise via a dropping funnel over 3 hrs. The time of the start of the dropwise addition was considered to be the time of the initiation of the polymerization, and the polymerization reaction was allowed to proceed for 6 hrs. After completing the polymerization, the polymerization solution was cooled to no greater than 30° C. via water-cooling. After cooling, the solution was charged into 1,000 g of methanol, and a white powder precipitated was filtered off. The filtered white powder was washed twice by slurrying in 200 g of methanol. Thereafter, filtration and drying at 60° C. for 17 hrs gave the polymer (CA-3) as a white powder (35.6 g; yield: 71%; Mw: 6,500; Mw/Mn: 1.48). The result of $^{13}$C-NMR analysis indicated that the ratio of the structural unit derived from the monomer (M-1):the structural unit derived from the monomer (M-2):the structural unit derived from the monomer (M-5) was 10.1:38.5:51.4 (mol %).

Preparation of Radiation-Sensitive Resin Composition

The acid generator (B) and the acid diffusion control agent and the solvent used in the preparation of the radiation-sensitive resin composition are shown below.

(B) Acid Generator
B-1: triphenylsulfonium perfluorobutanesulfonate
Acid Diffusion Control Agent
C-1: N-t-butoxycarbonyl-4-hydroxypiperidine
Solvent
D-1: propylene glycol monomethyl ether acetate
D-2: cyclohexanone
D-3: γ-butyrolactone Example 5

A radiation-sensitive resin composition was prepared by: mixing 100 parts by mass of (A-1), 8.4 parts by mass of (B-1) and 1 part by mass of (C-1), adding 900 parts by mass (D-1), 390 parts by mass of (D-2) and 30 parts by mass of (D-3) to the mixture to dissolve the mixture; and filtering the resulting mixed solution through a filter having a pore size of 0.20 μm.

Example 6

A radiation-sensitive resin composition was prepared by: mixing 100 parts by mass of (A-2), 8.4 parts by mass of (B-1) and 1 part by mass of (C-1), adding 900 parts by mass (D-1), 390 parts by mass of (D-2) and 30 parts by mass of (D-3) to the mixture to dissolve the mixture; and filtering the resulting mixed solution through a filter having a pore size of 0.20 μm.

Comparative Examples 1 to 3

Radiation-sensitive resin compositions of Comparative Examples 1 to 3 were prepared in a similar manner to Example 3 except that the polymer added as the component (A) blended in place of 100 parts by mass of (A-1) in Example 3 was: 100 parts by mass of (CA-1) in Comparative Example 1; 100 parts by mass of (CA-2) in Comparative Example 2; and 100 parts by mass of (CA-3) in Comparative Example 3.

Evaluations

The following performances were evaluated on the radiation-sensitive resin compositions prepared in Examples and Comparative Examples using an ArF excimer laser as a light source. The results are shown in Table 1.

Sensitivity

An underlayer antireflective film having a film thickness of 77 nm was provided on the surface of an 8 inch wafer using an agent for forming underlayer antireflective film (manufactured by Nissan Chemical Industries, Ltd., ARC29A). The radiation-sensitive resin composition of each of the Examples and Comparative Examples was spin-coated on the underlayer antireflective film, and PB was carried out on a hot plate at 100° C. for 60 sec to provide a resist coating film having a film thickness of 150 nm. The resist coating film was exposed through a mask pattern using a full-field projection aligner (manufactured by Nikon Corporation, S306C; numerical aperture: 0.78). Then after performing PEB for 60 sec at a PEB temperature shown in Table 1, the resist coating film was developed at 25° C. for 30 sec with a 2.38% by mass aqueous tetramethylammonium hydroxide solution, washed with water and dried to provide a resist pattern. The coating, the baking and the development in the foregoing were all carried out in-line using a coater/developer (manufactured by Tokyo Electron Limited, CLEAN TRACK ACT8). According to this procedure, an exposure dose (mJ/cm$^2$) at which the line width formed through a mask for a dimension of 75 nm with line-and-space of 1:1 resulted in formation of line-and-space of 1:1 with a line width of 75 nm was defined as an optimal exposure dose, and this optimal exposure dose was designated as sensitivity (mJ/cm$^2$). For line-width measurement, a scanning electron microscope (manufactured by Hitachi High-Technologies Corporation, 59260) was used.

LWR (Line Width Roughness)

Using the scanning electron microscope, a 75 nm 1:1 line-and-space pattern resolved at the optimum exposure dose was observed from above the pattern, and line widths at arbitrary ten points were measured. A 3 Sigma value that represents the degree of distribution of measurements of the line widths was defined as LWR (nm). Smaller LWR values indicate lead to evaluations of the formed pattern configuration being more favorable.

Number of Defects

The number of defects was inspected at a light-exposed site of the wafer produced in the determination of the Sensitivity. The number of defects was evaluated using a defect inspection system (manufactured by KLA-Tencor Corporation, KLA2351). The inspection of the number of defects was carried out by array-mode observation to detect the number of clustered/unclustered defects extracted from the difference resulting from pixel-unit superimposition with a reference image. Setting of the sensitivity of the defect inspection system was adjusted such that defects of no less than 0.15 μm can be detected. According to this inspection, the evaluation was made as "a" when the number of defects was no greater than 100 (counts/Wafer); and "B" when the number exceeded 100 (counts/Wafer).

TABLE 1

|  | Evaluation results | | | |
|---|---|---|---|---|
|  | PEB temperature (° C.) | sensitivity (mJ/cm²) | LWR (nm) | Number of defects |
| Example 5 | 95 | 20 | 8.5 | A |
| Example 6 | 95 | 19 | 8.0 | A |
| Comparative Example 1 | 95 | 22 | 9.5 | B |
| Comparative Example 2 | 95 | 20 | 8.8 | B |
| Comparative Example 3 | 115 | 21 | 11.0 | B |

From the results shown in Table 1, it was suggested that the radiation-sensitive resin composition of the embodiment of the present invention can form a resist pattern with less LWR, and accompanied by smaller number of defects, as compared with those of Comparative Examples.

According to the embodiment of the present invention, a radiation-sensitive resin composition being superior in an LWR property and capable of suppressing generation of defects, and a polymer and a compound suitably used for the composition and the like can be provided. Therefore, when used as a chemically amplified type radiation-sensitive resin composition that is sensitive to actinic radiation of a short wavelength, products with superior process margin in microfabrication can be manufactured. Therefore, these can be suitably used in the field of integrated circuit elements and the like in which microfabrication is expected to further advance in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition comprising a polymer having a structural unit represented by a formula (I):

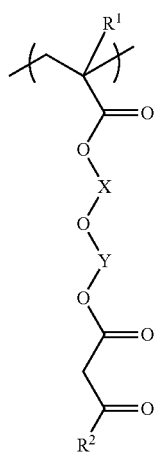

wherein, in the formula (I), $R^1$ represents a hydrogen atom or a methyl group; X represents a bivalent alicyclic hydrocarbon group not having or having a substituent; Y represents a bivalent hydrocarbon group having 1 to 20 carbon atoms; and $R^2$ represents a methyl group or a trifluoromethyl group.

2. The radiation-sensitive resin composition according to claim 1, wherein Y in the formula (I) represents an alkanediyl group having 2 to 4 carbon atoms.

3. The radiation-sensitive resin composition according to claim 1, further comprising a radiation-sensitive acid generator.

4. A polymer comprising a structural unit represented by a formula (I):

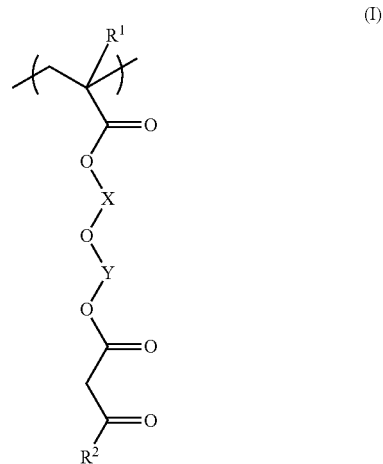

wherein, in the formula (I), $R^1$ represents a hydrogen atom or a methyl group; X represents a bivalent alicyclic hydrocarbon group not having or having a substituent; Y represents a bivalent hydrocarbon group having 1 to 20 carbon atoms; and $R^2$ represents a methyl group or a trifluoromethyl group.

5. A compound represented by a formula (i):

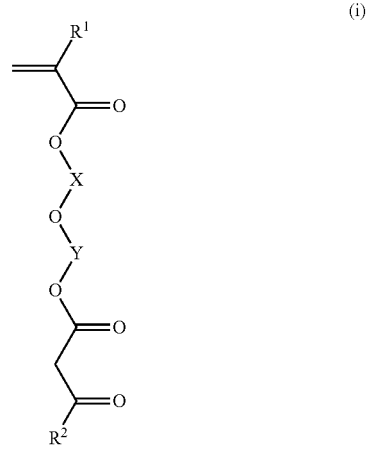

wherein, in the formula (i), $R^1$ represents a hydrogen atom or a methyl group; X represents a bivalent alicyclic hydrocarbon group not having or having a substituent; Y represents a bivalent hydrocarbon group having 1 to 20 carbon atoms; and $R^2$ represents a methyl group or a trifluoromethyl group.

* * * * *